US011971418B2

(12) United States Patent
Glezer et al.

(10) Patent No.: US 11,971,418 B2
(45) Date of Patent: Apr. 30, 2024

(54) GLOMERULONEPHRITIS BIOMARKERS

(71) Applicant: Meso Scale Technologies, LLC., Rockville, MD (US)

(72) Inventors: Eli N. Glezer, Del Mar, CA (US); John Kenten, Boyds, MD (US); Galina Nikolenko, Germantown, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 17/169,805

(22) Filed: Feb. 8, 2021

(65) Prior Publication Data

US 2021/0373033 A1    Dec. 2, 2021

Related U.S. Application Data

(62) Division of application No. 14/168,688, filed on Jan. 30, 2014, now abandoned.

(60) Provisional application No. 61/759,434, filed on Feb. 1, 2013.

(51) Int. Cl.
*G01N 33/68* (2006.01)

(52) U.S. Cl.
CPC ... *G01N 33/6893* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 5,208,535 A | 5/1993 | Nakayama et al. |
| 5,807,522 A | 9/1998 | Brown et al. |
| 6,110,426 A | 8/2000 | Shalon et al. |
| 7,842,246 B2 | 11/2010 | Wohlstadter et al. |
| 2003/0113713 A1 | 6/2003 | Glezer et al. |
| 2003/0207290 A1 | 11/2003 | Kenten et al. |
| 2004/0022677 A1 | 2/2004 | Wohlstadter et al. |
| 2004/0189311 A1 | 9/2004 | Glezer et al. |
| 2005/0052646 A1 | 3/2005 | Wohlstadter et al. |
| 2005/0142033 A1 | 6/2005 | Glezer et al. |
| 2006/0205012 A1 | 9/2006 | Debad et al. |
| 2014/0221325 A1 | 8/2014 | Glezer et al. |

FOREIGN PATENT DOCUMENTS

| | | |
|---|---|---|
| WO | 99/26067 A1 | 5/1999 |
| WO | 2004/058055 A2 | 7/2004 |
| WO | 2011/017680 A1 | 2/2011 |

OTHER PUBLICATIONS

El-Achkar et al. "Uormodulin in Kidney Injury: An Instigator, Bystander, or Protector?" (Mar. 2012) Am J Kidney Dis, 59(3): 452-461. (Year: 2012).*
Bauchet et al. "Immunochistochemical Identification of Kidney Nephron Segments in the Dog, Rat, Mouse, and Cynomolgus Monkey" (2011) Toxicology Pathology, 39: 1115-1128. (Year: 2011).*
Bauvois et al. "Specific changes in plasma concentrations of matrix metalloproteinases-2 and '9, TIMP-1, and TGF-B1 in patients with distinct types of primary glomerulonephritis." (2007), Nephrol Dial Transplant, vol. 22: 1115-1122. (Year: 2007).*
Akcay A. et al., "Mediators of Inflammation in Acute Kidney Injury", Mediators of Inflammation 2009:ID137072, pp. 1-12 (2009).
Appel G.B., "Glomerular Disorders and Nephrotic Syndromes", In: Goldman L. et al.,, Cecil Medicine 23rd Edition, Philadelphia, PA: Saunders Elsevier, Chapter 122 (13 pages) (2007).
Askenazi D.J. et al., "Baseline Values of Candidate Urine Acute Kidney Injury Biomarkers Vary by Gestational Age in Premature Infants", Pediatric Research 70(3):302-306 (2011).
Berns A., "Gene Expression in Diagnosis", Cancer 403:491-492 (2000).
Chen R. et al., "Simultaneous Quantification of Six Human Cytokines in a Single Sample Using Microparticle-Based Flow Cytometric Technology", Clinical Chemistry 45(9):1693-1694 (1999).
Delehanty J.B., "Printing Functional Protein Microarrays Using Piezoelectric Capillaries", Methods in Molecular Biology 264:135-143 (2004).
Devarajan P. et al., "Proteomics for Biomarker Discovery in Acute Kidney Injury", Semin Nephrol 27(6):637-651 (Nov. 2007).
Edelstein C.L., "Biomarkers of Acute Kidney Injury", Adv Chronic Kidney Des. 15(3):222-234 (Jul. 2008).
Hoffmann D. et al., "Evaluation of a Urinary Kidney Biomarker Panel in Rat Models of Acute and Subchronic Nephrotoxicity", Toxicology 277:49-58 (2010).
Hsiao R.J. et al., "Chromogranin A in Uremia: Progressive Retention of Immunoreactive Fragments", Kidney International 37:955-964 (1990).
Lawi W. et al., "A Microfluidic Cartridge System for Multiplexed Clinical Analysis", JALA Charlottesv Va. 14(6):407-412 (Dec. 1, 2009).
Lovett R.A., "Toxicogenomics: Toxicologists Brace for Genomics Revolution", Science 289(5479):536-537 (2000).
Lue R.Y.P. et al., "Site-Specific Immobilization of Biotinylated Proteins for Protein Microarray Analysis", Methods in Molecular Biology 264:85-100 (2004).
Parikh CR et al., "Urinary IL-18 is an Early Predictive Biomarker of Acute Kidney Injury After Cardia Surgery", Kidney International 70(1):199-203 (2006).

(Continued)

*Primary Examiner* — Teresa E Knight
(74) *Attorney, Agent, or Firm* — Scully, Scott, Murphy & Presser, P.C.

(57) ABSTRACT

The present invention relates to methods of diagnosing glomerulonephritis (GN) in a patient, as well as methods of monitoring the progression of GN and/or methods of monitoring a treatment protocol of a therapeutic agent or a therapeutic regimen. The invention also relates to assay methods used in connection with the diagnostic methods described herein.

20 Claims, 2 Drawing Sheets

(56) References Cited

OTHER PUBLICATIONS

Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (2000).
Skates S.J. et al., "Pooling of Case Specimens to Create Standard Serum Sets for Screening Cancer Biomarkers", Cancer Epidemiol Biomarkers Prev. 16(2):334-341 (2007).
Tramonti G. et al., "Relationship Between Renal Function and Blood Level of Chromogranin A", Renal Failure 23(3&4):449-457 (2001).
Vignali D.A.A., "Multiplexed Particle-Based Flow Cytometric Assays", Journal of Immunological Methods 243:243-255 (2000).
Walt D.R., "Molecular Biology: Bead-Based Fiber-Optic Arrays", Science 287(5452):451-452 (2000).
Wehr T. et al., "Experion™ Automated Electrophoresis System: Enhancing Sensitivity in SDS-Protein Electrophoresis", Bio-Rad Laboratories, Inc. Bulletin 5719:1-6 (2008).
MSD® 96-Well Multi-Array® and Multi-Spot® Human Cytokine Assays: Base Kit, MSD pp. 1-17 (Oct. 2009).
U.S. Final Office Action dated Feb. 6, 2020 received in U.S. Appl. No. 14/168,688.
U.S. non-Final Office Action dated Jul. 29, 2019 received in U.S. Appl. No. 14/168,688.
U.S. non-Final Office Action dated Oct. 17, 2018 received in U.S. Appl. No. 14/168,688.
U.S. Final Office Action dated Nov. 30, 2017 received in U.S. Appl. No. 14/168,688.
U.S. non-Final Office Action dated May 18, 2017 received in U.S. Appl. No. 14/168,688.
U.S. non-Final Office Action dated Oct. 28, 2016 received in U.S. Appl. No. 14/168,688.
U.S. Final Office Action dated Jan. 20, 2019 received in U.S. Appl. No. 14/168,688.
U.S. non-Final Office Action dated Jul. 7, 2015 received in U.S. Appl. No. 14/168,688.

\* cited by examiner

Figure 1

Figure 2

GLOMERULONEPHRITIS BIOMARKERS

CROSS REFERENCE TO RELATED APPLICATIONS

This application is a divisional of U.S. patent application Ser. No. 14/168,688 filed on Jan. 30, 2014, which claims the benefit of U.S. Provisional Application No. 61/759,434 filed on Feb. 1, 2013, the entire contents of which are incorporated herein by reference.

FIELD OF THE INVENTION

This application relates to assay methods useful in the detection and treatment of glomerulonephritis.

BACKGROUND OF THE INVENTION

Glomerulonephritis, also known as glomerular nephritis, abbreviated GN, is a renal disease (usually of both kidneys) characterized by inflammation of the glomeruli, or small blood vessels in the kidneys. GN is a type of renal disease in which the part of the kidneys that filter waste and fluids from the blood is damaged. Damage to the glomeruli causes blood and protein to be lost in the urine. While the exact cause of GN can be difficult to determine, it can be caused by immunological problems. GN can develop quickly, and kidney function can be lost within weeks or months (called rapidly progressive GN). A quarter of people with chronic GN have no history of kidney disease, but certain conditions can increase an individual's risk of developing GN, including but not limited to, blood or lymphatic system disorders, exposure to hydrocarbon solvents, and a history of cancer, infections such as strep infections, viruses, heart infections, or abscesses. Many conditions cause or increase the risk for GN, including amyloidosis, anti-glomerular basement membrane antibody disease, blood vessel diseases, such as vasculitis or polyarteritis, focal segmental glomerulosclerosis, goodpasture syndrome, heavy use of pain relievers, especially NSAIDs, Henoch-Schonlein purpura, IgA nephropathy, Lupus nephritis, and membranoproliferative GN.

SUMMARY OF THE INVENTION

The invention provides a method for evaluating the efficacy of a treatment regimen in a patient diagnosed with glomerulonephritis (GN), said method comprising
(a) obtaining a test sample from a patient undergoing said treatment regimen for GN;
(b) measuring a level of a biomarker in said test sample, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof;
(c) comparing said level to a normal control level of said biomarker; and
(d) evaluating from said comparing step (c) whether said patient is responsive to said treatment regimen.

In one embodiment, the invention includes a method for evaluating the efficacy of a treatment regimen in a patient diagnosed with glomerulonephritis (GN), said method comprising
(a) ordering a test comprising a measurement of a level of a biomarker in a test sample obtained from a patient undergoing said treatment regimen for GN, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof;
(b) comparing said level to a normal control level of said biomarker; and
(c) evaluating from said comparing step (b) whether said patient is responsive to said treatment regimen.

Moreover, the invention provides a method of administering a treatment regimen to a patient in need thereof for treating glomerulonephritis (GN), comprising:
(a) obtaining a test sample from a patient undergoing said treatment regimen for GN;
(b) measuring a level of a biomarker in said test sample, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof;
(c) comparing said level to a normal control level of said biomarker;
(d) evaluating from said comparing step (c) whether said patient is responsive to said treatment regimen; and
(e) adjusting said treatment regimen based on said evaluating step (d).

In addition, the invention contemplates a method of administering a treatment regimen to a patient in need thereof for treating glomerulonephritis (GN), comprising:
(a) obtaining a test sample from a patient prior to the commencement of said treatment regimen for GN;
(b) measuring a level of a biomarker in said test sample, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof;
(c) comparing said level to a normal control level of said biomarker;
(d) evaluating from said comparing step (c) whether said patient will be responsive to said treatment regimen; and
(e) administering said treatment regimen based on said evaluating step (d).

Still further, the invention includes a method of administering a treatment regimen to a patient in need thereof for treating glomerulonephritis (GN), comprising:
(a) evaluating a level of a biomarker in a test sample obtained from a patient undergoing said treatment regimen for GN relative to a normal control level of said biomarker, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof; and
(b) adjusting said treatment regimen based on said evaluating step (a).

Also provided is a method of administering a treatment regimen to a patient in need thereof for treating glomerulonephritis (GN), comprising:
(a) evaluating a level of a biomarker in a test sample obtained from a patient prior to the commencement of said treatment regimen for GN relative to a normal control level of said biomarker, wherein said biomarker comprises Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, SERPINB3, and combinations thereof; and (b) administering said treatment regimen based on said evaluating step (a).

Moreover, the invention provides a multiplexed assay kit used to evaluate the efficacy of a treatment regimen in a patient diagnosed with glomerulonephritis (GN), said kit is configured to measure a level of a plurality of biomarkers in a patient sample, said plurality of biomarkers comprises Clusterin, KIM-1, aGST, IL-6, CHGA, E-Cadherin, Timp-1, TNF-RI, TNF-RII, UMOD, and combinations thereof.

In one embodiment, a kit is provided for the analysis of a kidney disease panel comprising (a) a multi-well assay plate comprising a plurality of wells, each well comprising at least four discrete binding domains to which capture antibodies to the following human analytes are bound: Clusterin, KIM-1, aGST, IL-6, CHGA, E-Cadherin, Timp-1, INF-RI, TNF-RII, UMOD, and combinations thereof;

(b) in one or more vials, containers, or compartments, a set of labeled detection antibodies specific for said human analytes; and (c) in one or more vials, containers, or compartments, a set of calibrator proteins.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine. In a preferred embodiment, samples used in the assays of the invention are serum samples.

A "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes and/or to predict responsiveness or non-responsiveness to a particular therapeutic regimen). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit. A sample that is assayed in the diagnostic methods of the present invention may be obtained from any suitable patient, including but not limited to a patient suspected of having GN or a patient having a predisposition to GN. The patient may or may not exhibit symptoms associated with one or more of these conditions.

"Level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker or an additional biomarker in a sample.

As shown in Table 1, certain biomarkers were found to be altered in serum and urine GN patient samples:

TABLE 1

| Sample type | Change relative to normal control | Biomarker(s) |
| --- | --- | --- |
| Serum | elevated | Clusterin, KIM-1, aGST, IL-6, CHGA, E-Cadherin, Timp-1, TNF-RI and TNF-RII. |
|  | decreased | UMOD |
| Urine | elevated | OPGN, Calbindin, Clusterin, Osteoactin, Albumin, B2M, Cystatin C, NGAL, MCP-1, IL-6, IL-15, CHGA, E-Cadherin, ICAM-1, KDR, LBP, PRDX4, Prolactin, PSAT1, S100A4, TIMP-1, TNF-RI, TNF-RII and VCAM-1 |
|  | decreased | EGF, UMOD, and SERPINB3 |

In addition to the serum and urine biomarker levels, fractional excretion (FE) was assessed as a measure of the rate of excretion of the biomarker [FE=U/S[analyte]/U/S [creatinine]×100%]. Using FE, the following biomarkers were identified as having altered excretion rates in GN patients: OPGN, Calbindin, Clusterin, Osteoactivin, TFF3, B2M, Cystatin C, EGF, NGAL, MCP-1, IL-6, IL-8, IL-15, IL-7, SERPINB3, CHGA, ICAM-1, KDR, LBP, PRDX4, Prolactin, PSAT1, S100A4, TIMP-1, TNF-R1, TNF-RII and VCAM-1.

One or more of the biomarkers listed above can be used for the diagnosis of GN and/or to assess susceptibility of GN in a patient to a treatment regimen. For example, these biomarkers can be used in a diagnostic method, alone or in combination with other biomarkers for GN and/or diagnostic tests for GN, to diagnose GN in a patient. Alternatively or additionally, these biomarkers can be used to monitor a therapeutic regimen used for the treatment of GN to assess the efficacy of the regimen for a given patient.

The method of the present invention can include assessing the efficacy of a therapeutic regimen for GN and/or the susceptibility of a patient to a therapeutic regimen. In general, the goal of treatment for GN is to protect the kidneys from further damage and accordingly, one or more of the biomarkers listed above can be analyzed in combination with one or more biomarkers indicative of renal function, including but not limited to Lipocalin-2, osteopontin, albumin, TIM-1, NGAL, alpha GST, calbindin, clusterin, KIM-1, osteoactivin, TFF3, VEGF, cystatin C, EGF, OPN, and UMOD. Controlling a patient's blood pressure is critical to protecting the kidneys and slow the decline of kidney function. Accordingly, diuretics, angiotensin-converting enzyme (ACE) inhibitors, and/or angiotensin II receptor agonists can be used to protect the kidneys from further damage. If an underlying cause of GN has been identified, additional therapeutic agents can be administered, alone or in combination with one or more anti-hypertensive agents, including but not limited to: antibiotics (if GN resulted from a bacterial infection), corticosteroids and immunosuppressants (if GN resulted from Lupus or vasculitis), fish oil supplements and immunosuppressants (if GN resulted from IgA nephropathy), and plasmapheresis (if GN resulted from Goodpasture's syndrome). The biomarkers identified herein can be assessed before, during and/or after a treatment regimen including one or more such medications to assess disease progression.

Moreover, a therapeutic regimen may include administration of a therapeutic agent or a combination of therapeutic agents to a patient one or more times over a given time period. This treatment regimen may be accompanied by the administration of one or more additional therapeutic or palliative agents. The level(s) of biomarkers may be measured before treatment, one or more times during the administration period, and/or after treatment is suspended. Therefore, the method may include measuring an interim level of a biomarker during the therapeutic regimen and the method includes evaluating biomarker levels by comparing that level, the interim level and the baseline level. In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the method includes evaluating biomarker levels by comparing the level and the baseline level.

Still further, the method can include measuring a level(s) of a biomarker before a therapeutic regimen is initiated to predict whether GN will be responsive or non-responsive to a given therapeutic regimen. The method may further comprise modifying the therapeutic regimen based on the level(s) of a biomarker observed during this preliminary and/or interim measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

Still further, the method can include comparing the level of a biomarker to a detection cut-off level, wherein a level above the detection cut-off level is indicative of GN. Alternatively, the evaluating step comprises comparing a level of a biomarker to a detection cut-off level, wherein a level below the detection cut-off level is indicative of GN. In one embodiment of the present invention, the level of a biomarker is compared to a detection cut-off level or range, wherein the biomarker level above or below the detection cut-off level (or within the detection cut-off range) is indicative of GN. Furthermore, the levels of two or more biomarkers may both be used to make a determination. For example, i) having a level of at least one of the markers above or below a detection cut-off level (or within a detection cut-off range) for that marker is indicative of GN; ii) having the level of two or more (or all) of the markers above or below a detection cut-off level (or within a detection cut-off range) for each of the markers is indicative of GN; or iii) an algorithm based on the levels of the multiple markers is used to determine if GN is present.

The methods of the invention can be used alone or in combination with other diagnostic tests or methods to diagnose a patient with GN. The following tests/criteria are generally used by clinicians to diagnose a patient with GN, and this set of tests can be considered in combination with a diagnostic screen for the biomarkers identified herein to diagnose a patient with GN:

Clinical symptoms: anemia, high blood pressure, reduced kidney function, signs of chronic kidney disease may be seen, including: nerve inflammation (polyneuropathy), signs of fluid overload, including abnormal heart and lung sounds, edema;

Imaging tests: abdominal CT scan, kidney ultrasound, chest x-ray, intravenous pyelogram (IVP)

Urinalysis and other urine tests include: creatinine clearance, urine fortotal protein, uric acid in the urine; urine concentration test, urine creatinine, urine protein, urine RBC, urine specific gravity, urine osmolality Blood tests: albumin, anti-glomerular basement membrane antibody test, anti-neutrophil cytoplasmic antibodies (ANCAs), anti-nuclear antibodies, BUN and creatinine.

As described herein, the measured levels of one or more biomarkers may be used to detect or monitor GN and/or to determine the responsiveness of GN to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a disease and which reports such determination(s) back to the user.

According to one aspect of the invention, the level(s) of biomarker(s) are measured in samples collected from individuals clinically diagnosed with, suspected of having or at risk of developing GN. Initial diagnosis may be carried out using conventional methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, GN, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1-TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1-TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥0.8. In another embodiment, a biomarker provides an AUC≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric inter-quartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

The assays of the present invention may be conducted by any suitable method. In one embodiment, biomarker levels are measured in a single sample, and those measurement may be conducted in a single assay chamber or assay device, including but not limited to a single well of an assay plate, a single assay cartridge, a single lateral flow device, a single assay tube, etc. Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Yet al. Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000),403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, LE. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are commercially available (MULTI-SPOT® and MULTI-ARRAY® plates and SECTOR® instruments, Meso Scale Discovery, a division of Meso Scale Diagnostics, LLC, Rockville, Md.).

The present invention relates to a kit for the analysis of a panel of target analytes. The kit is preferably configured to conduct a multiplexed assay of two or more of the following analytes: Clusterin, KIM-1, aGST, IL-6, CHGA, E-Cadherin, Timp-1, TNF-RI, TNF-RII, UMOD, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, EGF, and SERPINB3, and combinations thereof. The kit can include (a) a single panel arrayed on a multi-well plate which is configured to be used in an electrochemiluminescence assay, as well as (b) associated consumables, e.g., detection antibodies, calibrators, and optional diluents and/or buffers. Alternatively, the multi-well plates and associated consumables can be provided separately.

The panel is preferably configured in a multi-well assay plate including a plurality of wells, each well having an array with "spots" or discrete binding domains. Preferably, the array includes one, four, seven, ten, sixteen, or twenty-five binding domains, and most preferably, the array includes one, four, seven, or ten binding domains. A capture antibody to each analyte is immobilized on a binding domain in the well and that capture antibody is used to detect the presence of the target analyte in an immunoassay. Briefly, a sample suspected of containing that analyte is added to the well and if present, the analyte binds to the capture antibody at the designated binding domain. The presence of bound analyte on the binding domain is detected by adding labeled detection antibody. The detection antibody also binds to the analyte forming a "sandwich" complex (capture antibody-analyte-detection antibody) on the binding domain.

The multiplexed immunoassay kits described herein allow a user to simultaneously quantify multiple biomarkers. The panels are selected and optimized such that the individual assays function well together. The sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

For a given panel, the detection antibody concentration and the number of labels per protein (L/P ratio) for the detection antibody are adjusted to bring the expected levels of all analytes into a quantifiable range at the same sample dilution. If one wants to increase the high end of the quantifiable range for a given analyte, then the L/P can be decreased and/or the detection antibody concentration is decreased. On the other hand, if one wants to increase the lower end of the quantifiable range, the L/P can be increased, the detection antibody concentration can be increased if it is not at the saturation level, and/or the background signal can be lowered.

Calibration standards for use with the assay panels are selected to provide the appropriate quantifiable range with the recommended sample dilution for the panel. The calibration standards have known concentrations of one of more of the analytes in the panel. Concentrations of the analytes in unknown samples are determined by comparison to these standards. In one embodiment, calibration standards comprise mixtures of the different analytes measured by an assay panel. Preferably, the analyte levels in a combined calibrator are selected such that the assay signals for each analyte are comparable, e.g., within a factor of two, a factor of five or a factor of 10. In another embodiment, calibration standards include mixtures of analytes from multiple different assay panels.

A calibration curve may be fit to the assay signals measured with calibration standards using, e.g., curve fits known in the art such as linear fits, 4-parameter logistic (4-PL) and 5-parameter (5-PL) fits. Using such fits, the concentration of analytes in an unknown sample may be determined by backfitting the measured assay signals to the calculated fits. Measurements with calibration standards may also be used to determine assay characteristics such as the limit of detection (LOD), limit of quantification (LOQ), dynamic range, and limit of linearity (LOL).

A kit can include the following assay components: a multi-well assay plate configured to conduct an immunoassay for one of the panels described herein, a set of detection antibodies for the analytes in the panel (wherein the set comprises individual detection antibodies and/or a composition comprising a blend of one or more individual detection antibodies), and a set of calibrators for the analytes in the panel (wherein the set comprises individual calibrator protein compositions and/or a composition comprising a blend of one or more individual calibrator proteins). The kit can also include one of more of the following additional components: a blocking buffer (used to block assay plates prior to addition of sample), an antibody diluent (used to dilute stock detection antibody concentrations to the working concentration), an assay diluent (used to dilute samples), a calibrator diluent (used to dilute or reconstitute calibration standards) and a read buffer (used to provide the appropriate environment for detection of assay labels, e.g., by an ECL measurement). The antibody and assay diluents are selected to reduce background, optimize specific signal, and reduce assay interference and matrix effect. The calibrator diluent is optimized to yield the longest shelf life and retention of calibrator activity. The blocking buffer should be optimized to reduce background. The read buffer is selected to yield the appropriate sensitivity, quantifiable range, and slowest off-rate.

The reagent components of the kit can be provided as liquid reagents, lyophilized, or combinations thereof, diluted or undiluted, and the kit includes instructions for appropriate preparation of reagents prior to use. In a preferred embodiment, a set of detection antibodies are included in the kit comprising a plurality of individual detection antibody compositions in liquid form. Moreover, the set of calibrators provided in the kit preferably comprise a lyophilized blend of calibrator proteins. Still further, the kit includes a multi-well assay plate that has been pre-coated with capture antibodies and exposed to a stabilizing treatment to ensure the integrity and stability of the immobilized antibodies.

As part of a multiplexed panel development, assays are optimized to reduce calibrator and detection antibody non-specific binding. In sandwich immunoassays, specificity mainly comes from capture antibody binding. Some considerations for evaluating multiplexed panels include: (a) detection antibody non-specific binding to capture antibodies is reduced to lower background of assays in the panel, and this can be achieved by adjusting the concentrations and L/P of the detection antibodies; (b) non-specific binding of detection antibodies to other calibrators in the panel is also undesirable and should be minimized; (c) non-specific binding of other calibrators in the panel and other related analytes should be minimized; if there is calibrator non-specific binding, it can reduce the overall specificity of the assays in the panel and it can also yield unreliable results as there will be calibrator competition to bind the capture antibody.

Different assays in the panel may require different incubation times and sample handling requirements for optimal performance. Therefore, the goal is to select a protocol that's optimized for most assays in the panel. Optimization of the assay protocol includes, but is not limited to, adjusting one or more of the following protocol parameters: timing (incubation time of each step), preparation procedure (calibrators, samples, controls, etc.), and number of wash steps.

The reagents used in the kits, e.g., the detection and capture antibodies and calibrator proteins, are preferably subjected to analytical testing and meet or exceed the specifications for those tests. The analytical tests that can be used to characterize kit materials include but are not limited to, CIEF, DLS, reducing and/or non-reducing EXPERION, denaturing SDS-PAGE, non-denaturing SDS-PAGE, SEC-MALS, and combinations thereof. In a preferred embodiment, the materials are characterized by CIEF, DLS, and reducing and non-reducing EXPERION. One or more additional tests, including but not limited to denaturing SDS-PAGE, non-denaturing SDS-PAGE, SEC-MALS, and combinations thereof, can also be used to characterize the materials. In a preferred embodiment, the materials are also subjected to functional testing, i.e., a binding assay for the target analyte, as well as one or more characterization tests, such as those listed above. If the materials do not meet or exceed the specifications for the functional and/or characterization tests, they can be subjected to additional purification steps and re-tested. Each of these tests and the metrics applied to the analysis of raw materials subjected to these tests are described below:

Capillary Isoelectric Focusing (CIEF) is a technique commonly used to separate peptides and proteins, and it is useful in the detection of aggregates. During a CIEF separation, a capillary is filled with the sample in solution and when voltage is applied, the ions migrate to a region where they become neutral (pH=pI). The anodic end of the capillary sits in acidic solution (low pH), while the cathodic end sits in basic solution (high pH). Compounds of equal isoelectric points (pI) are "focused" into sharp segments and remain in their specific zone, which allows for their distinct detection based on molecular charge and isoelectric point. Each specific antibody solution will have a fingerprint CIEF that can change over time. When a protein solution deteriorates, the nature of the protein and the charge distribution can change. Therefore, CIEF is a particularly useful tool to assess the relative purity of a protein solution and it is a preferred method of characterizing the antibodies and calibrators in the plates and kits described herein. The metrics used in CIEF include pI of the main peak, the pI range of the solution, and the profile shape, and each of these measurements are compared to that of a reference standard.

Dynamic Light Scattering (DLS) is used to probe the diffusion of particulate materials either in solution or in suspension. By determining the rate of diffusion (the diffusion coefficient), information regarding the size of particles, the conformation of macromolecular chains, various interactions among the constituents in the solution or suspension, and even the kinetics of the scatterers can be obtained without the need for calibration. In a DLS experiment, the fluctuations (temporal variation, typically in a μs to ms time scale) of the scattered light from scatterers in a medium are recorded and analyzed in correlation delay time domain.

Like CIEF, each protein solution will generate a fingerprint DLS for the particle size and it's ideally suited to detect aggregation. All IgGs, regardless of binding specificity, will exhibit the same DLS particle size. The metrics used to analyze a protein solution using DLS include percentage polydispersity, percentage intensity, percentage mass, and the radius of the protein peak. In a preferred embodiment, an antibody solution meets or exceeds one or more of the following DLS specifications: (a) radius of the antibody peak: 4-8 nm (antibody molecule size); (b) polydispersity of the antibody peak: <40% (measure of size heterogeneity of antibody molecules); (c) intensity of the antibody peak: >50% (if other peaks are present, then the antibody peak is the predominant peak); and (d) mass in the antibody peak: >50%.

Reducing and non-reducing gel electrophoresis are techniques well known in the art. The EXPERION™ (Bio-Rad Laboratories, Inc., www.bio-rad.com) automated electrophoresis station performs all of the steps of gel-based electrophoresis in one unit by automating and combining electrophoresis, staining, destaining, band detection, and imaging into a single step. It can be used to measure purity. Preferably, an antibody preparation is greater 50% pure by Experion, more preferably, greater than 75% pure, and most preferably greater than 80% pure. Metrics that are applied to protein analysis using non-reducing Experion include percentage total mass of protein, and for reducing Experion they include percentage total mass of the heavy and light chains in an antibody solution, and the heavy to light chain ratio.

Multi-Angle Light Scattering (MALS) detection can be used in the stand-alone (batch) mode to measure specific or non-specific protein interactions, as well as in conjunction with a separation system such as flow field flow fractionation (FFF) or size exclusion chromatography (SEC). The combined SEC-MALS method has many applications, such as the confirmation of the oligomeric state of a protein, quantification of protein aggregation, and determination of protein conjugate stoichiometry. Preferably, this method is used to detect molecular weight of the components of a sample.

As used herein, a lot of kits comprise a group of kits comprising kit components that meet a set of kit release specifications. A lot can include at least 10, at least 100, at least 500, at least 1,000, at least 5,000, or at least 10,000 kits and a subset of kits from that lot are subjected to analytical testing to ensure that the lot meets or exceeds the release specifications. In one embodiment, the release specifications include but are not limited to kit processing, reagent stability, and kit component storage condition specifications. Kit processing specifications include the maximum total sample incubation time and the maximum total time to complete an assay using the kit. Reagent stability specifications include the minimum stability of each reagent component of the kit at a specified storage temperature. Kit storage condition specifications include the range of storage temperatures for all components of the kit, the maximum storage temperature for frozen components of the kit, and the maximum storage temperature for non-frozen components of the kit. A subset of kits in a lot is reviewed in relation to these specifications and the size of the subset depends on the lot size. In a preferred embodiment, for a lot of up to 300 kits, a sampling of 4-7 kits are tested; for a lot of 300-950 kits, a sampling of 8-10 kits are tested; and for a lot of greater than 950 kits, a sampling of 10-12 kits are tested. Alternatively or additionally, a sampling of up to 1-5% preferably up to 1-3%, and most preferably up to 2% is tested.

In addition, each lot of multi-well assay plates is preferably subjected to uniformity and functional testing. A subset of plates in a lot is subjected to these testing methods and the size of the subset depends on the lot size. In a preferred embodiment, for a lot of up to 300 plates, a sampling of 4-7 plates are tested; for a lot of 300-950 plates, a sampling of 8-10 plates are tested; and for a lot of greater than 950 plates, a sampling of 10-12 plates are tested. Alternatively or additionally, a sampling of up to 1-5% preferably up to 1-3%, and most preferably up to 2% is tested. The uniformity and functional testing specifications are expressed in terms of %CV, Coefficient of Variability, which is a dimensionless number defined as the standard deviation of a set of measurements, in this case, the relative signal detected from binding domains across a plate, divided by the mean of the set.

One type of uniformity testing is protein A/G testing. Protein A/G binding is used to confirm that all binding domains within a plate are coupled to capture antibody. Protein A/G is a recombinant fusion protein that combines IgG binding domains of Protein A and protein G and it binds to all subclasses of human IgG, as well as IgA, IgE, IgM and, to a lesser extent, IgD. Protein A/G also binds to all subclasses of mouse IgG but not mouse IgA, IgM, or serum albumin, making it particularly well suited to detect mouse monoclonal IgG antibodies without interference from IgA, IgM, and serum albumin that might be present in the sample matrix. Protein A/G can be labeled with a detectable moiety, e.g., a fluorescent, chemiluminescent, or electrochemiluminescent label, preferably an ECL label, to facilitate detection. Therefore, if capture antibody is adhered to a binding domain of a well, it will bind to labeled protein A/G, and the relative amount of capture antibody bound to the surface across a plate can be measured.

In addition to the uniformity testing described above, a uniformity metric for a subset of plates within a lot can be calculated to assess within-plate trending. A uniformity metric is calculated using a matrix of normalized signals from protein A/G and/or other uniformity or functional tests. The raw signal data is smoothed by techniques known in the art, thereby subtracting noise from the raw data, and the uniformity metric is calculated by subtracting the minimum signal in the adjusted data set from the maximum signal.

In a preferred embodiment, a subset of plates in a lot is subjected to protein A/G and functional testing and that subset meet or exceed the following specifications:

TABLE 2

Plate Metrics

| Metric | Preferred Specification for a subset of 96 well multi-well plates |
|---|---|
| Average intraplate CV | ≤10% |
| Maximum intraplate CV | ≤13% |
| Average Uniformity | ≤25% |
| Maximum Uniformity | ≤37% |
| CV of intraplate averages | ≤18% |
| Signal, lower boundary | >1500 |
| Signal, upper boundary | $<10^{(6)}$ |

As disclosed in U.S. Pat. No. 7,842,246 to Wohlstadter et al., the disclosure of which is incorporated herein by reference in its entirety, each plate consists of several elements, e.g., a plate top, a plate bottom, wells, working electrodes, counter electrodes, reference electrodes, dielectric materials, electrical connects, and assay reagents. The wells of the plate are defined by holes/openings in the plate top. The plate bottom can be affixed, manually or by automated means, to the plate top, and the plate bottom can serve as the bottom of the well. Plates may have any number of wells of any size or shape, arranged in any pattern or configuration, and they can be composed of a variety of different materials. Preferred embodiments of the invention use industry standard formats for the number, size, shape, and configuration of the plate and wells. Examples of standard formats include 96, 384, 1536, and 9600 well plates, with the wells configured in two-dimensional arrays. Other formats may include single well plates (preferably having a plurality of assay domains that form spot patterns within each well), 2 well plates, 6 well plates, 24 well plates, and 6144 well plates. Each well of the plate includes a spot pattern of varying density, ranging from one spot within a well to 2, 4, 7, 9, 10, 16, 25, etc., as described hereinabove.

Each plate is assembled according to a set of preferred specifications. In a preferred embodiment, a plate bottom meets or exceeds the following specifications:

TABLE 3

Plate bottom specifications

| Parameter | 96-well (round well) specifications in inches |
| --- | --- |
| Length range (C to C)* | 3.8904-3.9004 (A1-A12 and H1-H12) |
| Width range (C to C) | 2.4736-2.4836 (A1-A12 and H1-H12) |
| Well to well spacing | 0.3513-0.3573 |

*C to C well distance is the center of spot to center of spot distance between the outermost wells of a plate.

In a further preferred embodiment, the plate also meets or exceeds defined specifications for alignment of a spot pattern within a well of the plate. These specifications include three parameters: (a) Δx, the difference between the center of the spot pattern and the center of the well along the x axis of the plate (column-wise, long axis); (b) Δy, the difference between the center of the spot pattern and the center of the well along the y axis of the plate (row-wise, short axis); and (c) α, the counter-clockwise angle between the long axis of the plate bottom and the long axis of the plate top of a 96-well plate. In a preferred embodiment, the plate meets or exceeds the following specifications: Δx≤0.2 mm, Δy≤0.2 mm, and α≤0.1°.

The following non-limiting examples serve to illustrate rather than limit the present invention.

EXAMPLES

Measurement of Biomarkers Indicative of Glomerulonephritis

Urine and serum samples were collected from 23 patients previously diagnosed with GN and 6 normal control subjects (patients having normal kidney function). Samples were analyzed in an immunoassay format and the samples were screened for the presence/absence of the following set of biomarkers: AKR1 B1, AKR1C2, Albumin, ALP, ANXA1, B2M, BCL2L2, Calbindin, CHGA, Clusterin, CRYAB, Cystatin C, E-Cadherin, EGF, EOTAXIN, EOTAXIN-3, FABP5, GCLM, GLO1, GM-CSF, GPI, GSTM1, GSTM2, ICAM-1, IFN-gamma, IFN-gamma, IL-10, IL-12P70, IL-13, IL-15, IL-16, IL18, IL-1alpha, IL-1beta, IL-2, IL-4, IL-5, IL-6, IL-7, IL-8, IP-10, KDR, KIM-1, LBP, MAGEA4, MAPK14, MBD1, MCP-1, MCP-4, MDC, MIP-1B, NGAL, NME2, OCL, ODC1, ONN, OPGN, OPN, osteoactivin, Osteopontin, P-Cadherin, PPP2R4, PRDX4, Prolactin, PSAT1, RAC1, RANTES, S100A4, S100A6, SAT1, SERPINB3, SFN, SOST, TARC, TFF3, TIMP-1, TNF RI, TNF RII, TNF-alpha, UMOD, VCAM-1, VEGF and αGST.

In general, the assay format was as follows, (all consumables, reagents, and instruments referenced below were supplied by Meso Scale Discovery, Rockville, Md.): (1) block MSD MULTI-SPOT® plate for 1 hour with appropriate MSD® blocking solution and wash; (2) add 25 µl assay diluent to each well, if specified; (3) add 25 µl calibrator, or sample (diluted as appropriate) to each well; (4) incubate with shaking for 1-3 hours (time as specified) and wash the well; (5) add 25 µl labeled detection antibody solution to each well; (6) incubate with shaking for 1-2 hours (time as specified) and wash the well; (7) add 150 µl MSD read buffer to each well; (8) read plate immediately on MSD SECTOR® 6000 Reader.

Figure 1:
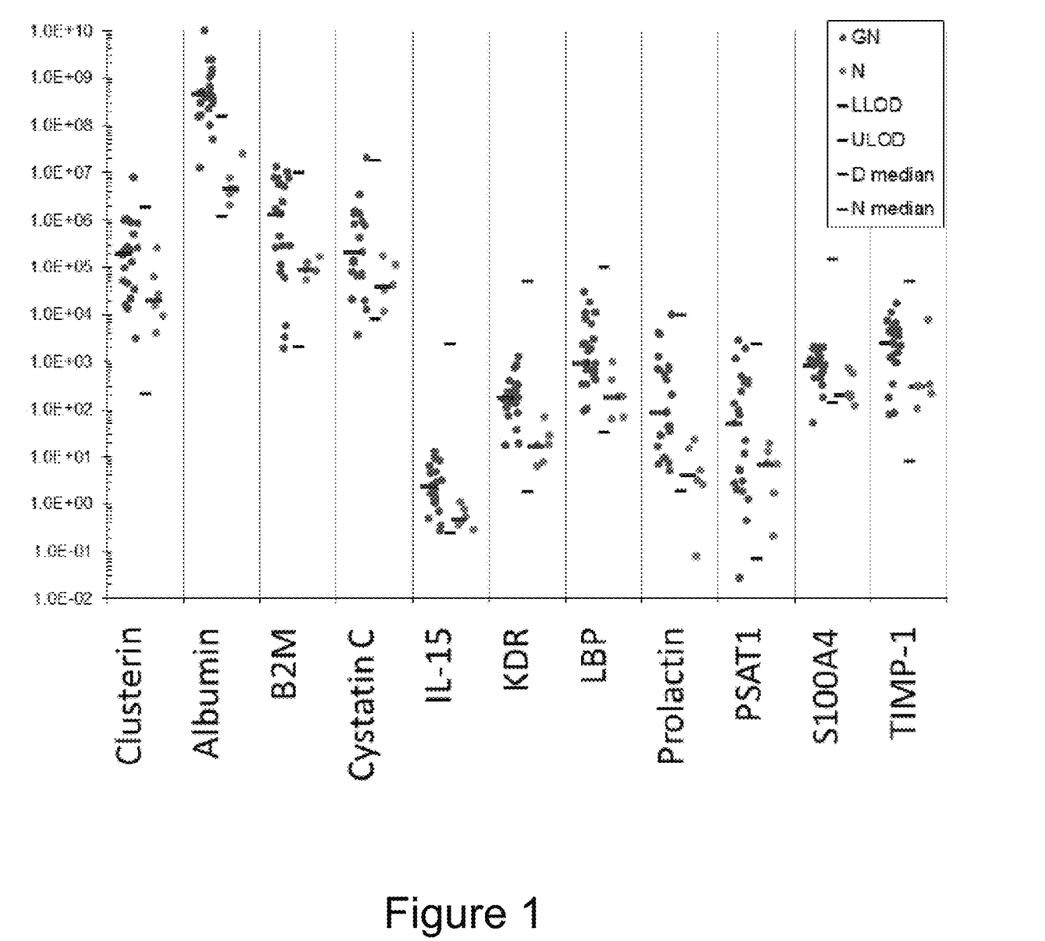
FIG. 1 shows elected urine biomarkers with elevated median levels in GN relative to patients with normal kidney function (N).

The following biomarkers were elevated in serum samples of GN patients relative to normal patients, Clusterin, KIM-1, aGST, IL-6, CHGA, E-Cadherin, Timp-1, TNF-RI and TNF-RII (Table 4). Lower serum levels of UMOD were also observed, a protein produced in the kidney (Henle's loop) and excreted in the urine, indicating kidney damage (Table 4, FIG. 1).

TABLE 4

Serum biomarkers with altered levels in GN relative to patients with normal kidney function (N). Median values are in pg/ml in serum.

| Biomarker | Clusterin | KIM-1 | aGST | UMOD | IL-6 | CHGA | E-Cadherin | Timp-1 | TNF-RI | TNF-RII |
| --- | --- | --- | --- | --- | --- | --- | --- | --- | --- | --- |
| median GN | 57,324,966 | 587 | 3,369 | 49,081 | 1.62 | 24,972 | 68,119 | 816,391 | 4,740 | 7,901 |
| median N | 25,705,457 | 211 | 1,640 | 122,308 | 0.41 | 7,306 | 26,247 | 258,562 | 2,004 | 2,966 |
| medGN/medN | 2.23 | 2.78 | 2.05 | 0.40 | 3.99 | 3.42 | 2.60 | 3.16 | 2.37 | 2.66 |

Figure 2:
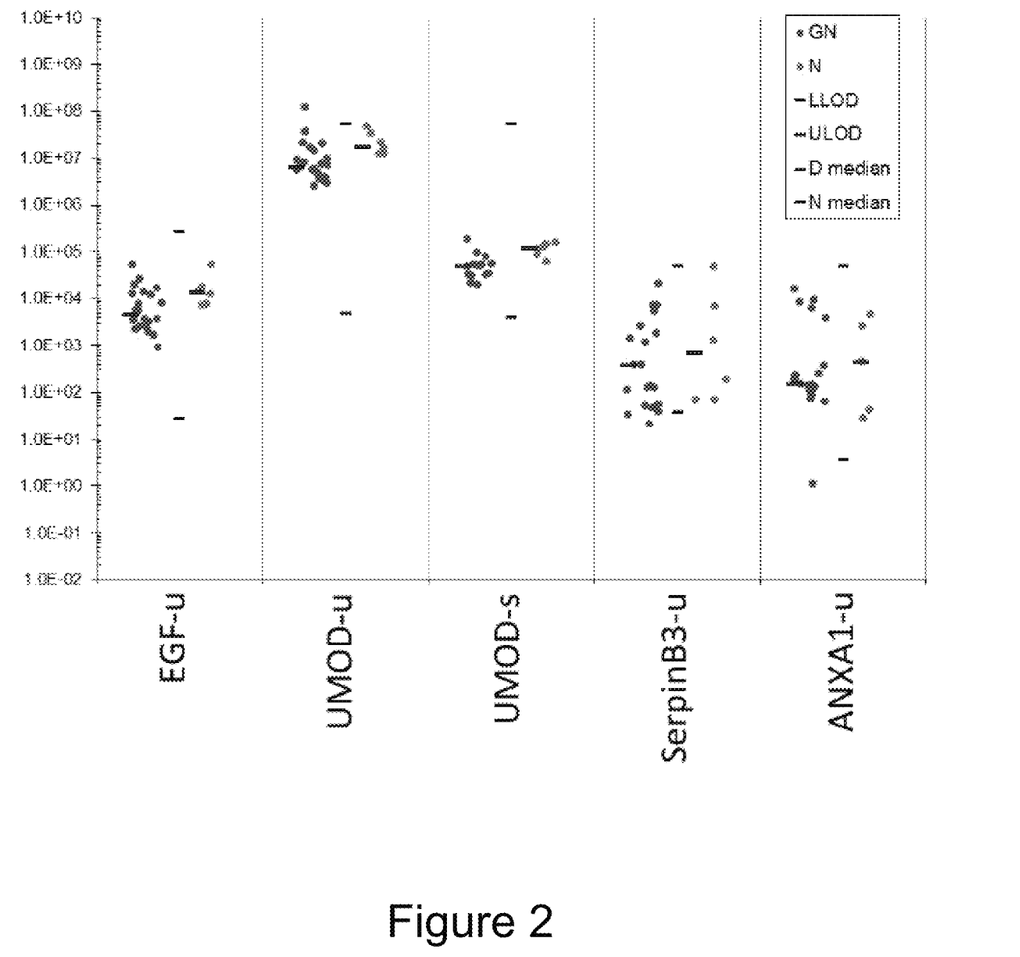
FIG. 2 shows biomarkers with lower median levels in GN patients relative to patients with normal kidney function (N) (biomarkers measured in urine samples are designated by the name of the biomarker followed by the designation "-u", e.g., EGF-u, UMOD-u, SerpinB3-u and ANXA1-u and serum UMOD-s).

In urine samples, a larger number of proteins with altered levels were identified, following normalization of these values to urine creatinine to correct for urine volume. The following biomarkers had elevated median values in GN patients: OPGN, Calbindin, Clusterin, Osteoactin, Albumin, B2M, Cystatin C, NGAL, MCP-1, IL-6, IL-15, CHGA, E-Cadherin, ICAM-1, KDR, LBP, PRDX4, Prolactin, PSAT1, S100A4, TIMP-1, TNF-RI, TNF-RII and VCAM-1 (Table 5, FIG. 1). The following biomarkers had lower levels, EGF, UMOD, SERPINB3 and ANXA1 (Table 5, FIG. 2).

TABLE 5

Urine biomarkers with altered levels in GN relative to patients with normal kidney function (N). Median normalized values were determined using the urine biomarker levels normalized to urine creatinine (normalized biomarker value = [pg/ml of biomarker]/[urine creatinine, mg/dl].

| Biomarker | OPGN | Calbindin | Clusterin | Osteoactin | Albumin | B2M | Cystatin C | EGF | NGAL | S100A4 |
|---|---|---|---|---|---|---|---|---|---|---|
| median GN | 0.86 | 87 | 996 | 18.57 | 3,758,615 | 14,241 | 917 | 50 | 849 | 8.25 |
| median N | 0.23 | 31 | 158 | 6.74 | 35,912 | 697 | 296 | 102 | 312 | 1.85 |
| medGN/medN | 3.67 | 2.78 | 6.29 | 2.76 | 105 | 20.42 | 3.10 | 0.49 | 2.72 | 4.46 |

| Biomarker | ANXA1 | CHGA | E-Cadherin | ICAM-1 | KDR | LBP | PRDX4 | Prolactin | PSAT1 |
|---|---|---|---|---|---|---|---|---|---|
| median GN | 1.59 | 0.90 | 119.24 | 48.88 | 1.98 | 10.02 | 23.16 | 1.08 | 0.35 |
| median N | 4.08 | 0.14 | 31.04 | 20.21 | 0.15 | 1.24 | 8.38 | 0.05 | 0.05 |
| medGN/medN | 0.39 | 6.53 | 3.84 | 2.42 | 13.51 | 8.06 | 2.76 | 23.48 | 7.20 |

| Biomarker | UMOD | MCP-1 | IL-6 | IL-15 | SERPINB3 | TIMP-1 | TNF-RI | TNF-RII | VCAM-1 |
|---|---|---|---|---|---|---|---|---|---|
| median GN | 70,843 | 3.03 | 0.022 | 0.017 | 2.69 | 13.88 | 46.64 | 91.68 | 26.70 |
| median N | 190,608 | 0.76 | 0.005 | 0.004 | 7.22 | 1.78 | 14.01 | 22.77 | 7.41 |
| medGN/medN | 0.37 | 3.98 | 4.56 | 4.42 | 0.37 | 7.79 | 3.33 | 4.03 | 3.61 |

As expected, the levels of albumin and other proteins were significantly elevated in urine, indicating damage to the kidney, allowing these proteins appear at elevated levels in the urine of GN patients. Although a general elevation of protein levels might have been expected across the biomarkers tested this did not prove to be the case, indicating that additional disease-specific diagnostic value was associated with these elevated biomarkers. In the case of the biomarkers with lower levels in the GN patients, these are of special interest since they contrast to the elevated protein levels anticipated in patients with damaged kidneys, and as such are especially valuable biomarkers for evaluating GN disease.

In addition to the serum and urine biomarker levels, the fractional excretion (FE) was calculated as a measure of the rate of excretion of a biomarker [FE=U/S[analyte]/U/S[creatinine]×100%]. Using FE, the following biomarkers were identified as having altered excretion rates in GN patients, OPGN, Calbindin, Clusterin, Osteoactivin, TFF3, B2M, Cystatin C, EGF, NGAL, MCP-1, IL-6, IL-8, IL-15, IL-7, SERPINB3, CHGA, ICAM-1, KDR, LBP, PRDX4, Prolactin, PSAT1, S100A4, TIMP-1, TNF-R1, TNF-RII and VCAM-1 (Table 6).

TABLE 6

Biomarkers with altered fractional excretion (FE) rates, in GN relative to patients with normal kidney function (N). Median normalized values were determined using the FE [FE = U/S[analyte]/U/S[creatinine] × 100%].

| Biomarker | OPGN | Calbindin | Clusterin | Osteoactivin | TFF3 | B2M | Cystatin C | EGF | NGAL |
|---|---|---|---|---|---|---|---|---|---|
| median GN | 87% | 124% | 0.42% | 10.90% | 25.77% | 42.53% | 40.16% | 2892% | 38% |
| median N | 12% | 42% | 0.05% | 1.90% | 9.53% | 2.87% | 2.34% | 11812% | 12% |
| medGN/medN | 7.26 | 2.94 | 9.07 | 5.73 | 2.70 | 14.83 | 17.16 | 0.24 | 3.06 |

| Biomarker | MCP-1 | IL-6 | IL-8 | IL-15 | IL-7 | SERPINB3 | CHGA | ICAM-1 | KDR |
|---|---|---|---|---|---|---|---|---|---|
| median GN | 102% | 372% | 174% | 199% | 32% | 55% | 0.83% | 4.58% | 1.32% |
| median N | 23% | 68% | 69% | 23% | 14% | 223% | 0.19% | 1.15% | 0.07% |
| medGN/medN | 4.43 | 5.50 | 2.53 | 8.71 | 2.21 | 0.25 | 4.28 | 4.00 | 17.82 |

| Biomarker | LBP | PRDX4 | Prolactin | PSAT1 | S100A4 | TIMP-1 | TNF-R1 | TNF-RII | VCAM-1 |
|---|---|---|---|---|---|---|---|---|---|
| median GN | 0.36% | 12.75% | 7.35% | 1.31% | 4.60% | 0.47% | 323% | 232% | 1.00% |
| median N | 0.03% | 4.37% | 0.05% | 0.38% | 0.91% | 0.06% | 56% | 70% | 0.20% |
| medGN/medN | 13.4 | 2.9 | 143.6 | 3.41 | 5.06 | 7.38 | 5.77 | 3.32 | 5.00 |

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

REFERENCES

1. Appel G B. Glomerular disorders and nephrotic syndromes. In: Goldman L, Ausiello D, eds. Cecil Medicine. 23rd ed. Philadelphia, Pa: Saunders Elsevier; 2007:chap 122.
2. Nachman P H, Jennette J C, Falk R J. Primary glomerular disease. In: Brenner B M, ed. Brenner and Rector's The Kidney. 8th ed. Philadelphia, Pa.: Saunders Elsevier; 2007:chap 30.

The invention claimed is:

1. A method of detecting glomerulonephritis (GN) in a patient, comprising:
   (a) receiving a comparison of a normal control level of biomarkers versus a level of at least three or more of a plurality of biomarkers in a test sample obtained from a patient, said plurality of biomarkers selected from (i) a first group consisting of aGST, IL-6, CHGA, E-Cadherin, Timp-1, TNF-RI, and TNF-RII, and (ii) a second group consisting of EGF, UMOD, and SERPINB3, wherein at least one of said three biomarkers is a biomarker from the second group and at least one of said three biomarkers is a biomarker from the first group;
   (b) evaluating from said comparison that the patient has GN; and
   (c) administering a treatment regimen based on said evaluating step (b), wherein said treatment regimen comprises one or more of diuretics, angiotensin-converting enzyme (ACE) inhibitors, angiotensin II receptor agonists, antibiotics, corticosteroids, immunosuppressants, fish oil supplements, or plasmapheresis.

2. A method according to claim 1 wherein said comparison comprises conducting a multiplexed assay of said plurality of said biomarkers in said test sample, wherein said multiplexed assay is conducted using one reaction volume comprising said test sample.

3. The method of claim 1 wherein said method comprises receiving a comparison of a normal control level of biomarkers versus a level of at least four or more of said plurality of biomarkers.

4. The method of claim 1 wherein said method further comprises receiving a comparison of a normal control level of biomarkers versus a level of an additional biomarker comprising Clusterin, KIM-1, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, and combinations thereof.

5. A method of claim 4 wherein said additional biomarker is one or both of: Clusterin, and KIM 1.

6. The method of claim 1 further comprising determining from said level of said biomarkers the disease progression of GN.

7. The method of claim 1, wherein said sample comprises serum and wherein said method further comprises receiving a comparison of a normal control level of biomarkers versus a level of an additional biomarker comprising Clusterin, KIM 1, and combinations thereof.

8. The method of claim 1, wherein said sample comprises urine and wherein said method further comprises receiving a comparison of a normal control level of biomarkers versus a level of an additional biomarker comprising OPGN, Calbindin, Clusterin, Osteoactin, Albumin, B2M, Cystatin C, NGAL, MCP-1, IL-15, ICAM-1, KDR, LBP, PRDX4, Prolactin, PSAT1, S100A4, VCAM 1, and combinations thereof.

9. The method of claim 1 wherein said sample comprises serum and/or urine and wherein said method further comprises receiving a comparison of a normal control level of biomarkers versus a level of an additional biomarker comprising OPGN, Calbindin, Clusterin, Osteoactivin, TFF3, B2M, Cystatin C, EGF, NGAL, MCP-1, IL-6, IL-8, IL-15, IL-7, SERPINB3, CHGA, ICAM-1, KDR, LBP, PRDX4, Prolactin, PSAT1, S100A4, TIMP-1, TNF-R1, TNF-RII, VCAM-1 and combinations thereof.

10. The method of claim 9 wherein said method further comprises determining fractional excretion of said biomarkers.

11. A method of treating glomerulonephritis (GN) in a patient, comprising:
    (a) receiving a comparison of a normal control level of biomarkers versus a level of at least three or more of a plurality of biomarkers in a test sample obtained from a patient prior to the commencement of a treatment regimen for GN, said plurality of biomarkers selected from (i) a first group consisting of aGST, IL-6, CHGA, E-Cadherin, Timp-1, TNF-RI, and TNF-RII, and (ii) a second group consisting of EGF, UMOD, and SERPINB3, wherein at least one of said three biomarkers is a biomarker from the second group and at least one of said three biomarkers is a biomarker from the first group;
    (b) evaluating from said comparison that the patient will be responsive to a treatment regimen; and
    (c) administering said treatment regimen based on said evaluating step (b), wherein said treatment regimen comprises one or more of diuretics, angiotensin-converting enzyme (ACE) inhibitors, angiotensin II receptor agonists, antibiotics, corticosteroids, immunosuppressants, fish oil supplements, or plasmapheresis.

12. The method according to claim 11 wherein said comparison comprises conducting a multiplexed assay of said plurality of said biomarkers in said test sample, wherein said multiplexed assay is conducted using one reaction volume comprising said test sample.

13. The method of claim 11 wherein said method comprises receiving a comparison of a normal control level of biomarkers versus a level of at least four or more of said plurality of biomarkers.

14. The method of claim 11 wherein said method further comprises receiving a comparison of a normal control level of biomarkers versus a level of an additional biomarker comprising Clusterin, KIM-1, OPGN, Calbindin, Osteoactin, Albumin, B2M, Cystatin C, NGAL, MCP-1, IL-15, ICAM-1, KDR, LBP, PRDX4, Prolactin, PSAT1, S100A4, TIMP-1, VCAM-1, and combinations thereof.

15. The method of claim 14 wherein said additional biomarker is one or both of selected from: Clusterin, and KIM-1.

16. The method of claim 11 further comprising determining from said level of said biomarkers the disease progression of GN.

17. The method of claim 11 wherein said sample comprises serum and wherein said method further comprises receiving a comparison of a normal control level of biomarkers versus a level of an additional biomarker comprising Clusterin, KIM-1, and combinations thereof.

18. The method of claim 11 wherein said sample comprises urine and wherein said method further comprises receiving a comparison of a normal control level of biomarkers versus a level of an additional biomarker comprising OPGN, Calbindin, Clusterin, Osteoactin, Albumin, B2M, Cystatin C, NGAL, MCP-1, IL-15, ICAM-1, KDR, LBP, PRDX4, Prolactin, PSAT1, S100A4, VCAM-1, and combinations thereof.

19. The method of claim 11 wherein said sample comprises serum and/or urine and wherein said method further comprises receiving a comparison of a normal control level of biomarkers versus a level of an additional biomarker comprising OPGN, Calbindin, Clusterin, Osteoactivin, TFF3, B2M, Cystatin C, EGF, NGAL, MCP-1, IL-6, IL-8, IL-15, IL-7, SERPINB3, CHGA, ICAM-1, KDR, LBP, PRDX4, Prolactin, PSAT1, S100A4, TIMP-1, TNF-R1, TNF-RII, VCAM-1 and combinations thereof.

20. The method of claim 19 wherein said method further comprises determining fractional excretion of said biomarkers.

* * * * *